US006958063B1

(12) United States Patent
Soll et al.

(10) Patent No.: US 6,958,063 B1
(45) Date of Patent: *Oct. 25, 2005

(54) PLASMA GENERATOR FOR RADIO FREQUENCY SURGERY

(75) Inventors: Joachim Soll, Pinneberg (DE); Klaus Zobawa, Elmshorn (DE); Buu Son Trinh, Hamburg (DE); Holger Soring, Quickborn (DE)

(73) Assignee: Soring GmbH Medizintechnik, Quickborn (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/557,906

(22) Filed: Apr. 21, 2000

(30) Foreign Application Priority Data

Apr. 22, 1999 (DE) .......................................... 199 18 315

(51) Int. Cl.[7] .............................................. A61B 18/18
(52) U.S. Cl. ............................. 606/41; 606/32; 606/34; 606/45; 606/49
(58) Field of Search ............................... 606/32, 34, 38, 606/40, 41, 42, 49; 219/121.5, 121.36, 121.48, 121.54, 121.51

(56) References Cited

U.S. PATENT DOCUMENTS

| 3,903,891 A | | 9/1975 | Brayshaw |
|---|---|---|---|
| 3,958,883 A | | 5/1976 | Turner |
| 4,250,373 A | | 2/1981 | Tanida |
| 4,369,919 A | | 1/1983 | Beloev et al. |
| 4,781,175 A | | 11/1988 | McGreevy et al. |
| 5,115,168 A | | 5/1992 | Shoda et al. |
| 5,130,003 A | | 7/1992 | Conrad |
| 5,207,675 A | * | 5/1993 | Canady .................... 606/40 |
| 6,010,499 A | * | 1/2000 | Cobb ........................ 606/40 |
| 6,013,075 A | * | 1/2000 | Avramenko et al. ........ 606/40 |

FOREIGN PATENT DOCUMENTS

| DE | 79087 | | 1/1971 |
|---|---|---|---|
| EP | 0155496 | | 1/1991 |
| EP | 0787465 | | 8/1997 |
| EP | 0837622 | | 4/1998 |
| WO | WO 98/35618 | * | 8/1998 |

* cited by examiner

*Primary Examiner*—David M. Shay
(74) *Attorney, Agent, or Firm*—Horst M. Kasper

(57) ABSTRACT

The present invention furnishes a plasma generator for generating a cold plasma jet beam in the application field of medicine and in particular of surgery as well as other fields of science. The plasma generator is furnished with a separate, frequency tunable oscillator, wherein the frequency tunable oscillator controls the power end stage through a driver stage. The radio frequency of the outpout of the generator is determined by a resonance frequency of a resonance transformer. The plasma current is limited by a capacitor disposed in the hand piece.

41 Claims, 14 Drawing Sheets

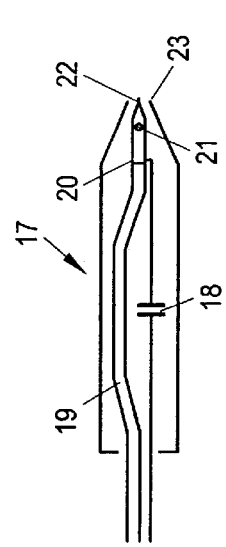
Fig.2
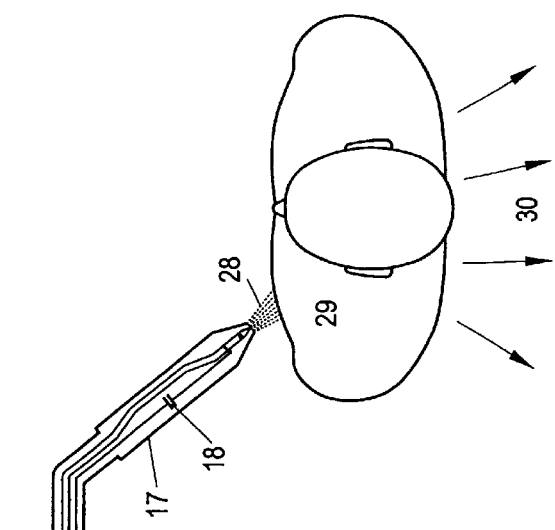
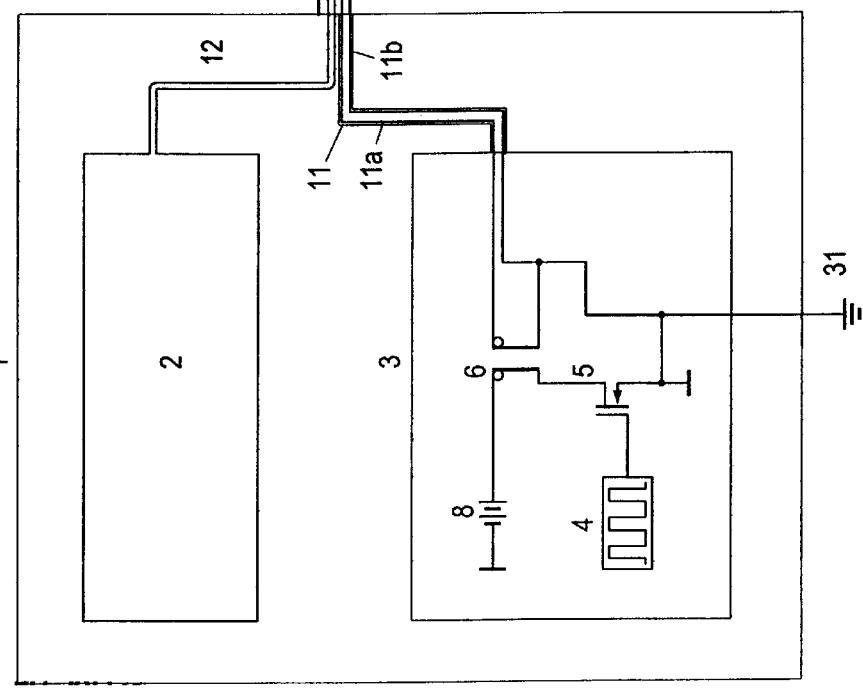
Fig.1

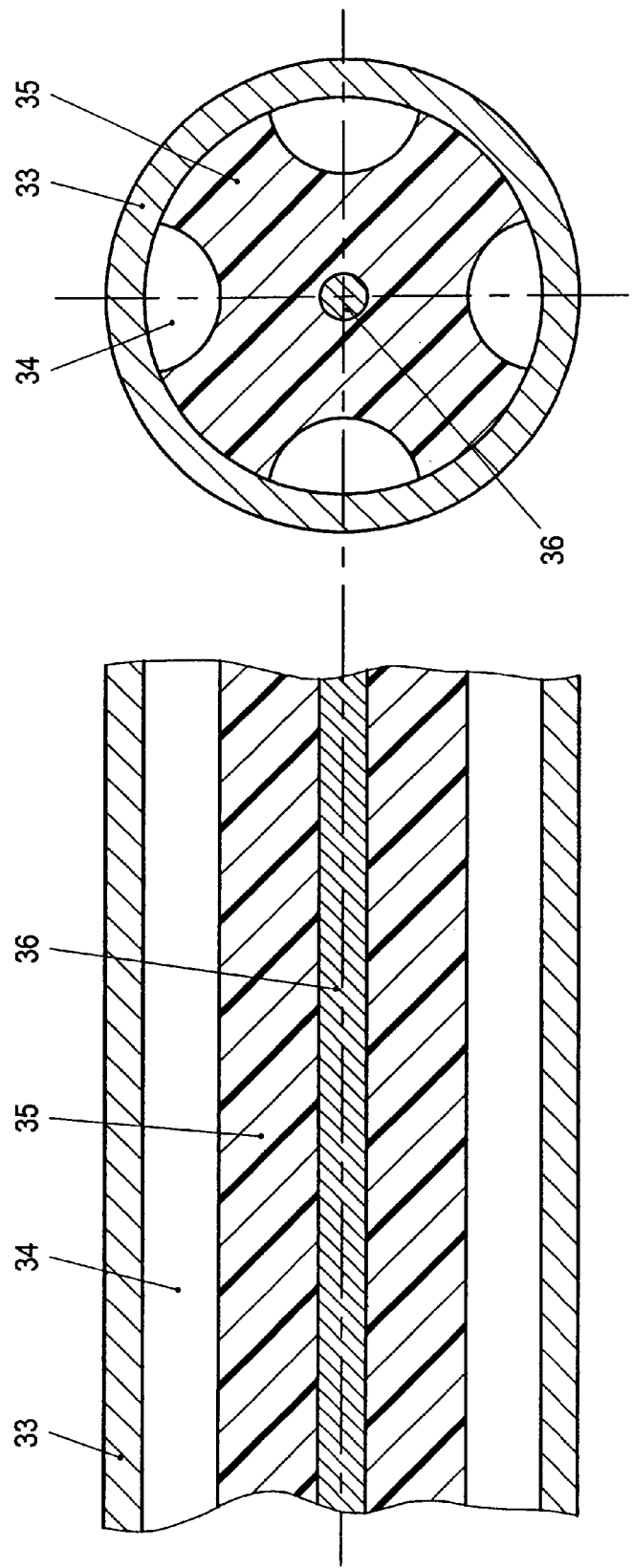

PLASMA GENERATOR FOR RADIO FREQUENCY SURGERY

BACKGROUND OF THE INVENTION

1. Field of the Invention

The present Invention relates to a plasma generator for generating a cold plasma jet beam in the application field of medicine and in particular of surgical applications as well as in other fields of science.

2. Brief description of the Background of the Invention Including Prior Art

Plasma sources, which are capable of generating a plasma under atmospheric pressure conditions and having a temperature of above 1000 degrees centigrade belong to the general state of the art. The heating of a plasma is effected by classic electromagnetic induction, and in fact by the inductive heating of electrically conducting media in an alternating electromagnetic field of an induction coil. This plasma source comprises a high voltage alternating current generator, a tubular shaped quartz container and a liquid cooled induction coil, wherein the induction coil exhibits a large number of windings. A coil of 10 cm diameter is absolutely necessary to be furnished with many windings in order to be able to generate an induction in a volume of about one liter. The inductive resistance increases with frequencies of more than 1 MHz very much. It is difficult in general to adapt the high voltage generator to the inductive resistance because the effective output power is thereby decreased. The development of a plasma source according to the state-of-the-art effect leads to a reduction of the dimensions, however, also to a lesser effectiveness and to high plasma temperatures, which means a limitation of the field of application in particular in the field of medicine, biology and ecological treatments.

Other plasma generators are employed in electrical discharge apparatus, wherein the electrical discharge apparatus is equipped with an electronic oscillator, a modulation unit, a resonance transformer, and a rod shaped discharge electrode. A plasma jet beam is generated here between the end of the electrode and the object. The electronic oscillator generates oscillations of the order of magnitude of from about two hundred to 300 kHz. The modulator switches the oscillator signal on and off in a frequency region of from about three kHz to 5 kHz. Thus the modulator generates a densified excitation of the resonance transformer and of the object. This apparatus leads to a favorable therapeutic effect for the treatment of numerous illnesses mainly by applying heat to certain regions of the body.

This apparatus has however uncovered insufficiencies of the kind that the discharge transformation from the corona to the shape of the spark becomes visible and wherein the conduit leads directly into the tissue.

The classical corona and the spark discharge result unavoidably in ionization, electrical breakdown and heating of the air gap between the electrode and the body employed as a second electrode. A heat conditioned chaotic motion of particles in the discharge region is associated herewith.

The conventional radio frequency surgery works with a radio frequency generator in case of the spray coagulation or, respectively, argon coagulation (plasma discharge in an argon jet beam), wherein the radio frequency generator operates according to the method of shock impulse excitation and impact ionization of oscillating circuits. This impulse excitation of an oscillating circuit delivers short radio frequency pulses (bursts) with a pause interval of a relatively long time duration with respect to the pulse duration. The ratio pulse time duration/pause interval duration amounts to generally about 10 to 20 percent. This leads to a high peak power during the bursts and furthermore very high peak currents, which can reach several amperes. The capacity between patient and ground is insufficient under these conditions to close the current circuit. For this reason a neutral electrode is necessarily required in conventional radio frequency surgery. Furthermore the high currents result in a relatively large contact area of the electric arc on the tissue of several square millimeters and consequently are associated with a relatively large penetration depth of the heat effect. In addition, the flowing through of high peak currents through the tissue leads to a high current load even in larger depths, which can lead to damages at sensitive tissues, for example nerve tissue in the brain. The spectrum of a radio frequency current, which consists out of short bursts, comprises always a not to be underestimated part, which part is derived from the pulse repetition frequency. This frequency is generally in the range of between 10 and 70 kHz. These low frequencies can cause damage at sensitive tissues. Plasma generators of conventional kind, which generate the plasma inductively or by an arc discharge are too heavy because of the necessary cooling requirements for this purpose to be placed into a hand piece. Furthermore the conventional plasma generators exhibit a very high plasma temperature of up to several thousand degrees centigrade as a thermal plasma.

A further plasma generator is described in the European printed patent document EP-A 0837622. This generator comprises a voltage source, an electrical oscillator, wherein the electrical oscillator is furnished with an amplifier connected to a low voltage device, a resonance transformer furnished with a low voltage input and a high voltage output, and a connection of the high voltage output of the resonance transformer to the discharge electrode. This oscillator is furnished with a feedback winding, wherein the feedback winding is furnished for the operation with a single stage power oscillator. The very low stability of the discharge amplitude and the therewith associated problems of the power control are disadvantageous in connection with such a single stage oscillator.

U.S. Pat. No. 4,781,175 to McGreevy et al. teaches an electrosurgical conductive gas stream technique of achieving improved eschar for coagulation. A predetermined ionizable gas in a jet is conducted to the tissue at a predetermined flow rate sufficient to clear natural fluids from the tissue and to expose substantially the tissue stroma. To achieve fulguration electrical energy is conducted as arcs in the ionized conductive pathways.

The European patent application EP 0787465 A1 to Kim et al. teaches a cold plasma coagulator. The cold plasma coagulator of the reference includes a high frequency power supply, a gas dynamic block and a plasmotron. The power supply includes a rectifier, a capacitor storage and a voltage inverter. A resonance inductor and a dielectric tube are located coaxially with the one end of the dielectric tube being connected to the gas dynamic block and the second end of the dielectric tube in position to eject plasma through an output nozzle. The coils of the resonance inductor consist of a low voltage section and a high-voltage section, wherein the low voltage section of the resonance coils is connected to the output of the voltage inverter.

The German Democratic Republic patent 79087 to G. Pforr teaches a device for operating an inductive plasma torch. A high frequency alternating current derived from a high frequency generator is fed into an operating coil. The operating coil is disposed separately from the high frequency generator in an adjustable way and is connected by a power coaxial cable to the high frequency generator. An inductive plasma flame is generated within an insulating tube within the operating coil.

The European patent specification 0155496 to Peter Gagne teaches a plasma emissions source. The plasma emissions source comprises a radio frequency power generator, a plasma torch, means for automatically and continuously maximizing the radio frequency power transferred from the generator to a load coil. A series network and a shunt network are tunable for matching the impedance of the power generator and of the load coil. Each network includes at least one variable capacitor, a control means for driving the capacitors, wherein the control means includes a first motor means and a second motor means for driving said at least one capacitor of each network respectively, as well as a detector means for providing input signals representative of the phase relationship of the radio frequency voltage and the radio frequency current.

A hand piece for surgical cutting with a plasma jet beam is taught in U.S. Pat. No. 4,781,175 to Birtcher and shown in particular in FIGS. 6 to 9.

Conventional radio frequency surgery apparatus deliver unsteady signals exhibiting high current peaks of several amperes. These current peaks of conventional apparatus can cause damages also in deeper disposed tissue sections based on high electrical potential at the inside and at the outside of the cell membrane.

The recited problems of the known plasma generators have led in principle to a limitation in the application of electromagnetic technology in medicine and here particularly in the surgery field.

SUMMARY OF THE INVENTION

1. Purposes of the Invention

It is an object of this present invention to develop an alternative plasma generator for surgical applications, wherein the alternative plasma generator does not exhibit the recited problems of conventional plasma generators.

It is another object of the present invention to furnish an eschar with a cold plasma jet beam surgical appliance, wherein the eschar, if possible, does not exhibit any coking and carbonization products based on oxygen inclusions, as eschars can occur in connection with the argon plasma method.

These and other objects and advantages of the present invention will become evident from the description which follows.

2. Brief Description of the Invention

The present invention is directed to a cold plasma device to be used in radio frequency surgery for coagulation of tissue surfaces and for the removal abrading of tissue.

The cold plasma apparatus according to the present invention comprises a radio frequency generator, a resonance transformer, a hand piece and a gas supply for He.

The apparatus serves for coagulation of tissue by way of plasma discharge in the radio frequency surgery field with the following construction and features. A radio frequency generator delivers its signal to a resonance transformer. The resonance transformer transforms the radio frequency signal of about 350 kHz to a voltage level of from about 2000 to 3000 volts. The output of this resonance transformer (secondary winding) is connected to a hand piece through a coaxial conduit with integrated gas feed of Helium. The second pole of the secondary winding is grounded. The hand piece includes an electrode tip, wherein the electrode tip is disposed in a nozzle, wherein the nozzle is passed through by and is flown around by the protective gas He. This electrode tip is connected to the wire of the coaxial line conducting the radio frequency voltage through a capacitor. If the radio frequency generator is activated, then an immediate corona discharge is performed at the electrode tip within the nozzle. The gas current drives the corona discharge to the outside through the nozzle such that a flame discharge in air occurs. If this flame is directed toward a tissue, then an arc discharge is started to the tissue with a corresponding lighting arc appearance. The high current density occurring at the point of impingement as well as the acceleration of the charge carriers (ions) immediately at the impingement point of the electric light arc effect coagulation and an evaporation of the tissue in case the radio frequency has been selected to be sufficiently high.

The radio frequency current then flows as a dielectric displacement current from the surface of the patient to ground, as long as the patient is not electrically grounded. A neutral electrode is not employed and thereby a direct electrical current flow through the patient is prevented or, respectively, substantially reduced. The capacitor incorporated in the hand piece limits the radio frequency current to values below under 150 mA based on the small capacity of the capacitor such that the maximum permissible radio frequency leakage currents in radio frequency surgery will not be surpassed. The resonance transformer is not excited by pulses in contrast to conventional radio frequency surgical apparatus and the excitation of the resonance transformer is continuously performed. The resonance transformer thus delivers a pure sinusoidal signal without the high current peaks of several amperes present in conventional radio frequency surgery apparatus and these signals do not cause damages in deeper disposed tissue sections of the tissue.

The cutting effect in radio frequency surgery is based on the principal of cellular rupture. The obtained cuts can be distinguished as smooth cut, cut rich of coagulation and cut with eschar.

A smooth cut in radio frequency surgery is largely comparable to a cut obtained the conventional scalpel, that is the cutting surfaces are only slightly colored. The cutting mode of the smooth cut is achieved with an unmodulated radio frequency current and by carrying out the cut quickly.

A reduction of cutting speed provides a more coagulated cut or, respectively, a cut with an eschar. The same result is achieved when employing a pulse modulated radio frequency current with the same average power.

The power necessary for performing a radio frequency cut depends on the shape of the electrode, the type of the tissue and the resistance of the tissue. If the power is to low, then no cell rupture takes place and the tissue sticks to the electrode. If the applied power is too high then spark discharges in electrode and tissue are possible, which causes carbonization of the cut surfaces.

The tissue is heated more or less to such a degree that no cell rupture occurs for obtaining coagulation. The temperature of coagulation is above 50 degrees centigrade. This temperature leads to a coagulation of the intra-cellular and of the extra cellular albumine by boiling of the tissue. Perforated blood vessels contract to such extent that the vessel is totally closed and no blood flows out. In order to obtain this effect an electric current must heat the tissue at a sufficiently slow speed so that intra-cellular and extra cellular fluids are vaporized without destroying the cell membranes. The cells contract by loss of fluid and the cell walls are welded together. This kind of coagulation is frequently called contact coagulation because the electrodes are brought into direct contact with the tissue. A supply of radio frequency current causes a light coloring of the tissue and a flow out of tissue fluid due to cellular coagulation.

The present invention furnishes a separate oscillator usable with respect to frequency to the plasma generator for generating a cold plasma jet beam, wherein the oscillator controls a power end stage.

An embodiment of the plasma generator comprises that the output signal of the end stage operating as a switch is furnished to the primary winding of the ignition coil.

It is a further feature of the plasma generator that the phase difference between the oscillator signal and the output signal of the final stage is measured at the primary winding for tuning the oscillator frequency.

According to a further embodiment of the subject of the present invention a control system is furnished, wherein the oscillator frequency is tuned relative to the resonance frequency of the ignition coil by the control system.

In addition, the plasma generator includes an automatic control of the radio frequency performed by changing the operating voltage and wherein the power is captured by multiplying input current and the input voltage at the final stage.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention:

FIG. 1 shows a view of a schematic diagram illustrating a first embodiment of the plasma generator and of the hand piece, FIG. 2 shows a detail view of the hand piece according to FIG. 1, FIG. 10 is a sectional view of a first probe for endoscopy, FIG. 11 is a sectional view the first probe of endoscopy according to FIG. 10.

DESCRIPTION OF INVENTION AND PREFERRED EMBODIMENT

Figure 3:
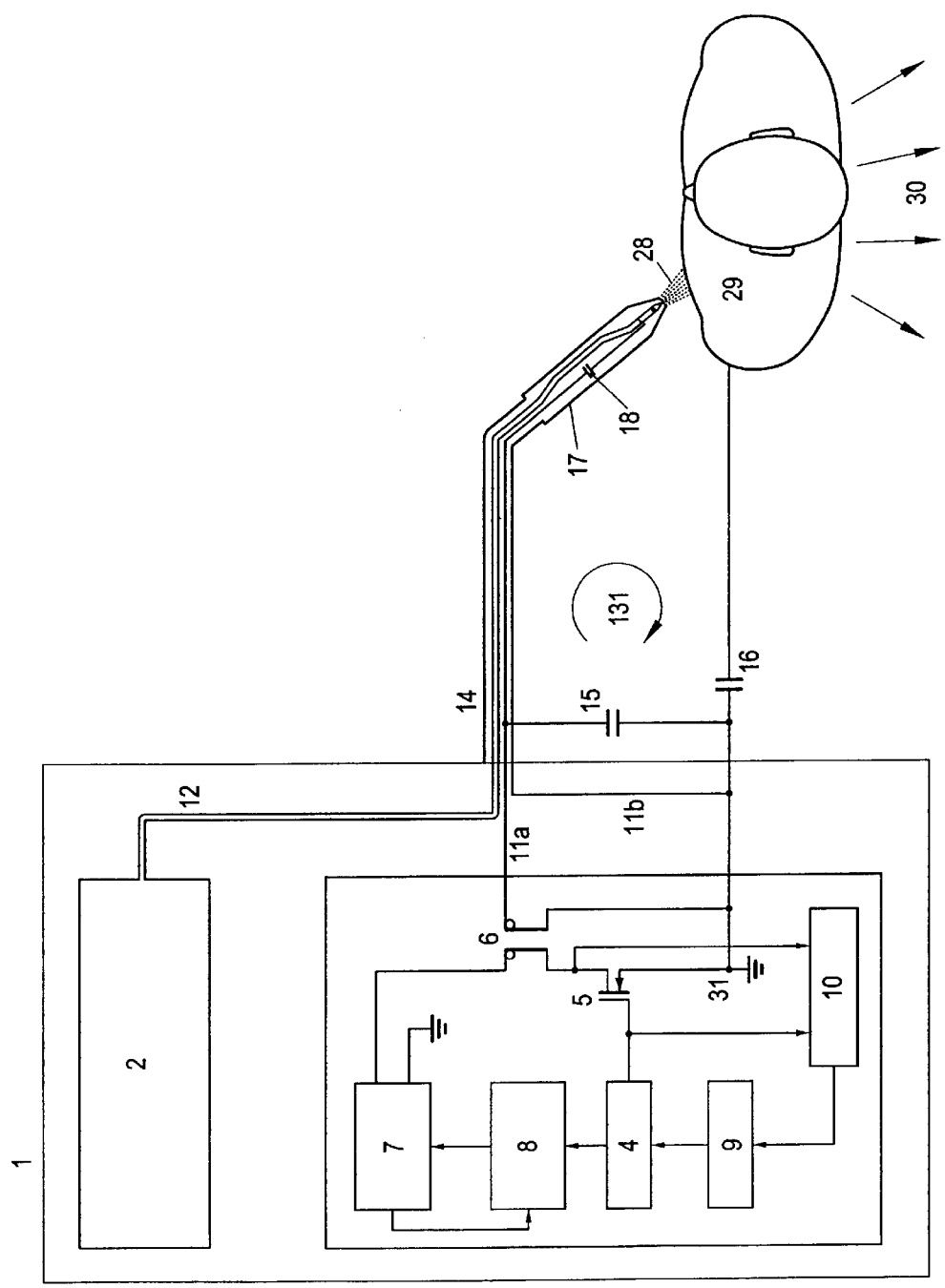
FIG. 3 shows a view of a schematic diagram of a second embodiment of a plasma generator employed in connection with a hand piece.

The radio frequency generator according to the present invention is connected directly to a resonance transformer. The radio frequency generator comprises a switching transistor, which periodically interrupts the operating voltage at the primary coil of the resonance transformer, an automatic device tuning the switching frequency of the transistor automatically to a resonance frequency of the resonance transformer, and a device for capturing the electrical power discharge at the resonance transformer for automatically controlling and delimiting the output power by variation of the operating voltage.

The system according to the present invention comprises a radio frequency generator 3, wherein the radio frequency generator 3 generates a radio frequency voltage with a switching transistor 5, a resonance transformer 6, wherein the radio frequency voltage is conducted through a coaxial line 11 and a capacitor 18 of small capacity of from about 5 to 50 pF to a metal tip 22. This metal tip 22 is disposed in a nozzle 23 at the end of a hand piece 17. At the same time an easily ionizable noble gas such as He is lead from a gas supply apparatus 2 not described in detail here through a gas tube 12 disposed in the cable 14 of the hand piece 17 into the hand piece 17. The gas supply apparatus 2 and the radio frequency generator form a supply module surrounded by casing 1. The gas line 19 joins within the hand piece into a metal tube 20 with the gas discharge openings 21 and the metal tip 22 (FIG. 2). The gas flows as a gas beam from the gas discharge openings 21 out of the nozzle 23. If the radio frequency generator is switched on, then the radio frequency current passes through the co-axial cable 11, the hand piece cable 14 and the capacitor 18 to the metal tip 22. In case of a sufficient radio frequency voltage, an electrical discharge occurs from the metal tip 22 onto the tissue surface 29 of the patient to be treated. The radio frequency current flows from the patient as a capacitive displacement current 30 to ground and passes the ground connection 31 back to the radio frequency generator. A neutral electrode as is employed in the conventional standard radio frequency surgery is here not required. Based on the specific construction of the radio frequency generator with a resonance transformer 6, wherein the secondary winding of the resonance transformer 6 forms a parallel oscillating circuit together with the capacity of the coaxial line 11 and wherein a nearly sinusoidal radio frequency voltage is generated by controlling the transistor 5 with the resonance frequency of the resonance transformer 6. The capacitor 18 disposed in the hand piece delimits the radio frequency current to sufficiently small values under 150 mA corresponding to the standard requirements generally imposed as they are relating to radio frequency surgery (IEC 601-2-2). The presence of the capacitor 18 forming a resonance circuit with the secondary winding of the resonance transformer 6 in connection with the limiting of the radio frequency current is important in connection with the present invention.

The relatively small radio frequency current of from about 20 to 100 mA depending on the capacity of the hand piece capacitor leads in the discharge channel to only a slight heating. Based on the very small impingement surface of the electric arc onto the tissue, where the diameter of the impingement surface amounts to only a few hundred micrometers, there is generated locally a very high current density, which very high current density locally leads to a strong heating of the tissue. This current density drops however already in a very small distance from the impingement point of the electric arc to values, which values would not lead any longer to any observable heating of the tissue. Since the radio frequency essentially flows off from the patient to ground as a capacitive displacement current, an electrical current flow through tissues and thereby possibly damaging deeper disposed tissue layers is thereby prevented.

If the electric arc is lead in a quick sequence over the tissue surface, then the tissue surface is coagulated with a very small penetration depth. A point shaped application, where the electric arc essentially hits always the same position, leads to such a strong heating of the tissue surface that the tissue practically is evaporated. This method allows to evaporate tissue from the surface of the tissue.

Referring now to FIG. 3 there is shown an oscillator 4 supplying a rectangular pulse voltage to the transistor 5. This transistor 5 switches and applies the voltage delivered by the automatically controllable voltage source 8 and the power capture/power limiter 7 periodically to the primary winding of the resonance transformer 6. This resonance transformer 6 contains a primary winding with a few windings from about 3 to 30 as well as a secondary winding with many windings from about 50 to 1000 and preferably from about 100 to 500, which are wound onto a ferrite core with an air gap. The capacity 15 (FIG. 3) of the coaxial line in the hand cable 14 forms a resonance circuit together with the secondary winding of the resonance transformer 6. If the transistor 5 is controlled with the resonance frequency of the transformer 6, then the secondary winding of the resonance transformer 6 delivers a high sinusoidal radio frequency voltage with values of from about 2000 to 4000 volts. The radio frequency current passes to an electrode 22 formed as a tip through the hand piece capacitor 18 disposed in the hand piece 17. An easily ionizable gas such as He is led through the tube 12 in the hand piece cable to the electrode tip 22, wherein the electrode tip 22 is disposed in and/or protrudes from the nozzle 23. The high radio frequency voltage causes a plasma discharge as an electric arc 28 toward the tissue surface of the patient 29. The patient forms the stray capacity 16 relative to the ground. The radio frequency current flows through this stray capacity and through the ground potential back to the resonance transformer 6. The position with reference numeral 131 shows schematically the course of the current.

The impedance of the electric arc depends on the length of the electric arc and on the radio frequency current. The electric arc impedance falls strongly in case of a high current density in the electric arc. This requires a limitation of the radio frequency current. This limitation is effected by the impedance of the hand piece capacitor 18 (FIGS. 1 and 2). The hand piece capacitor 18 is furnished with a capacity of preferably from about 10 to 50 pF depending on the desired radio frequency current. In case of a generator frequency of about 350 kHz this results in an impedance value of from about 9 to 45 kohm. In case of a voltage of 3000 volts there are resulting currents from about 65 to 330 mA. However only currents in the region of from about 40 to 120 mA are measured because of the generally fairly high impedance of the electric arc.

The high resonance quality of the resonance transformer 6 requires an excitation with the exact resonance frequency. The impedance derived from the hand piece capacitor 18 and derived from the electric arc influences the resonance frequency of the resonance transformer 6. This leads to a heavy drop-off of the resonance frequency at the time when the plasma discharge is started. This resonance drop off varies depending on the discharge conditions within the electric arc 28. Therefore an exact frequency control of the oscillator relative to the actual resonance frequency of the resonance transformer 6 is necessary. A difference between the actual resonance frequency and the oscillator frequency is observable in the change of the phase angle between the oscillator signal and the signal at the primary winding of the resonance transformer 6. The phase comparison stage 10 compares the two phase positions relative to each other and delivers the actual value to the automatic frequency control circuit 9 (FIG. 3). If the phase angle deviates from the predetermined value for an exact coincidence with the resonant frequency, then the oscillator frequency is correspondingly corrected by a control signal.

In case a high electrical power is delivered to the electric arc 28, then the power acceptance of the end stage including transistor 5 (FIGS. 1 and 3) also rises. A surpassing of the limiting value of the radio frequency current, through operating means of the apparatus not illustrated here, effects at reduction of the direct current delivered by the automatically controllable voltage source 8 by way of an electrical control signal.

Figure 4:
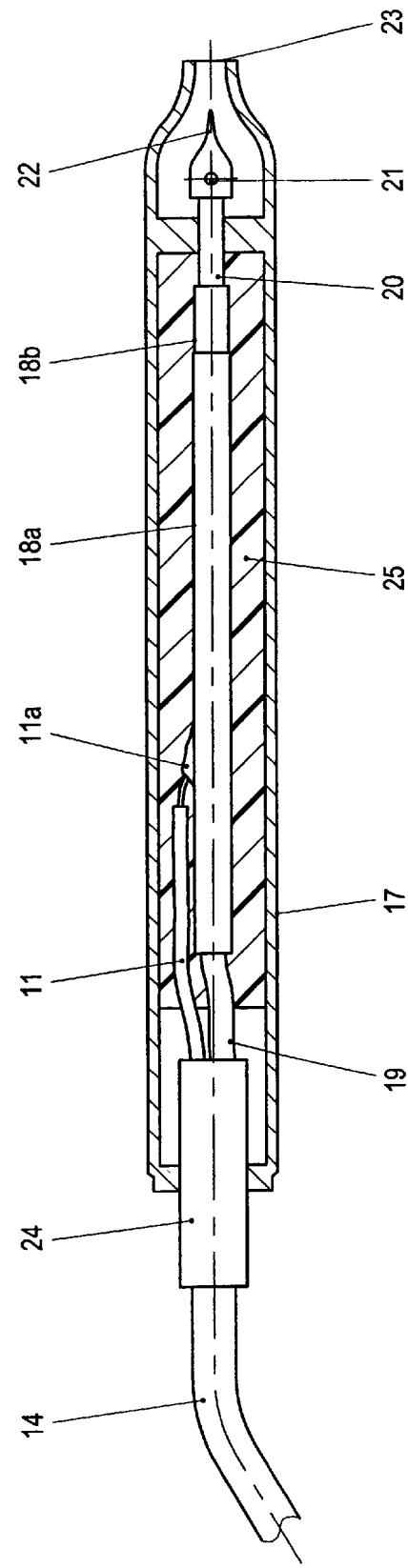
FIG. 4 shows a sectional view of a first hand piece.
Figure 5:
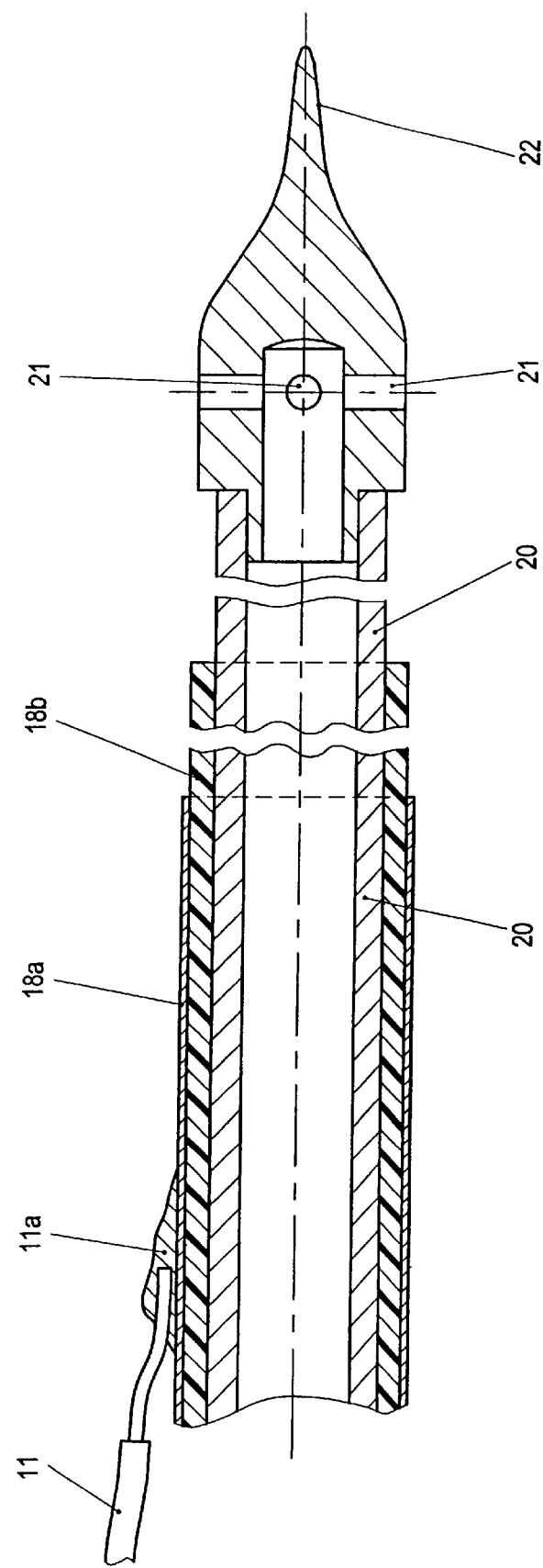
FIG. 5 is a sectional view of the electrode tip positioned in the hand piece.

The hand piece 17 is shown in detail in FIGS. 4 and 5. An easily ionizable gas such as He passes through a tube conduit 19 from the hand piece cable 14 into the metal tube 20. The easily ionizable gas passes through a gas discharge opening 21 into the nozzle 23 and leaves the hand piece 17 as a beam.

The radio frequency voltage delivered by the resonance transformer 6 passes through a coaxial line disposed in the hand piece cable to a metalization 18a disposed on top of an isolating layer formed by a dielectric 18b. For example a silicon tube is employed as a dielectric, wherein the silicon tube is slid onto the metal tube 20. A thin metal foil, which thin metal foil for example is made of copper, can be employed to furnish the metalization 18a (FIG. 4). The wire of the coaxial cable is connected to the metalization in the region 11a, for example by soldering.

The metalization 18a on the dielectric 18b (FIG. 5) forms together with the metal tube 20 a capacitor, wherein the capacitor as mentioned above serves for limiting the current of the plasma discharge. Depending on the construction and the dimensions of the metal tube, of the isolating layer and of the length of the metalization there can be realized capacities falling into a range of from about 2.5 to 150 pF and preferably falling into a range of from about 5 to 50 pF. The current of the plasma discharge and thereby the plasma power can be adapted to the desired purpose of application of the hand piece. Capacities of substantially more than 50 pF will deliver in general such intense plasma currents, which plasma currents are too high for surgical purposes.

Figure 6:
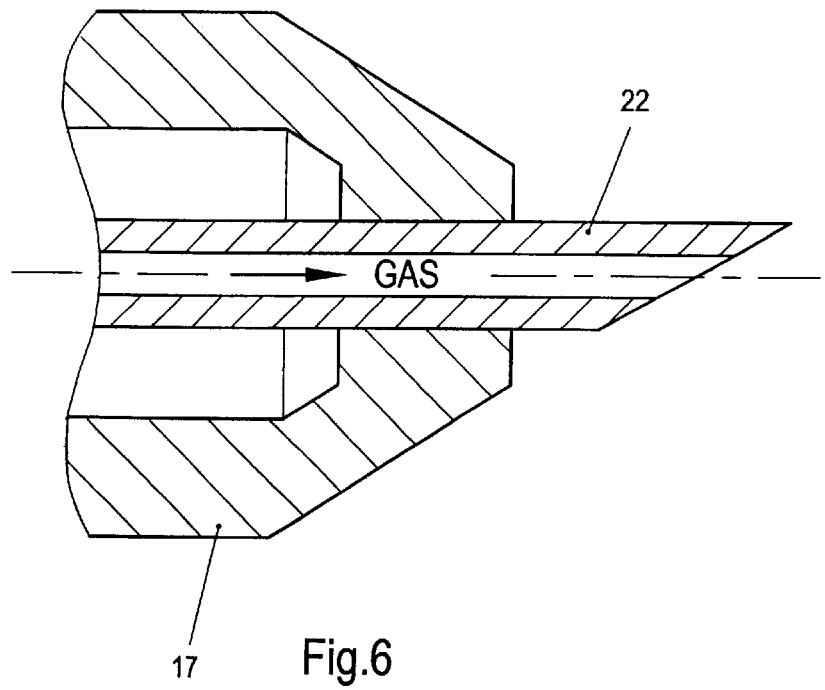
FIG. 6 is a sectional view of an inclined metal tube with a gas discharge, wherein the metal tube serves at the same time as an electrode.
Figure 7:
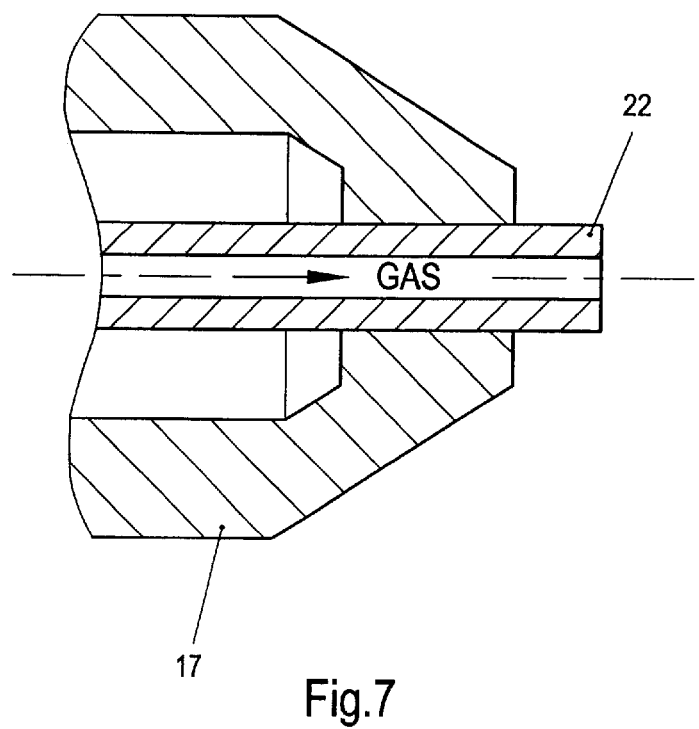
FIG. 7 is a sectional view of a straight metal tube with a gas discharge, wherein the metal tube serves at the same time as an electrode.
Figure 8:
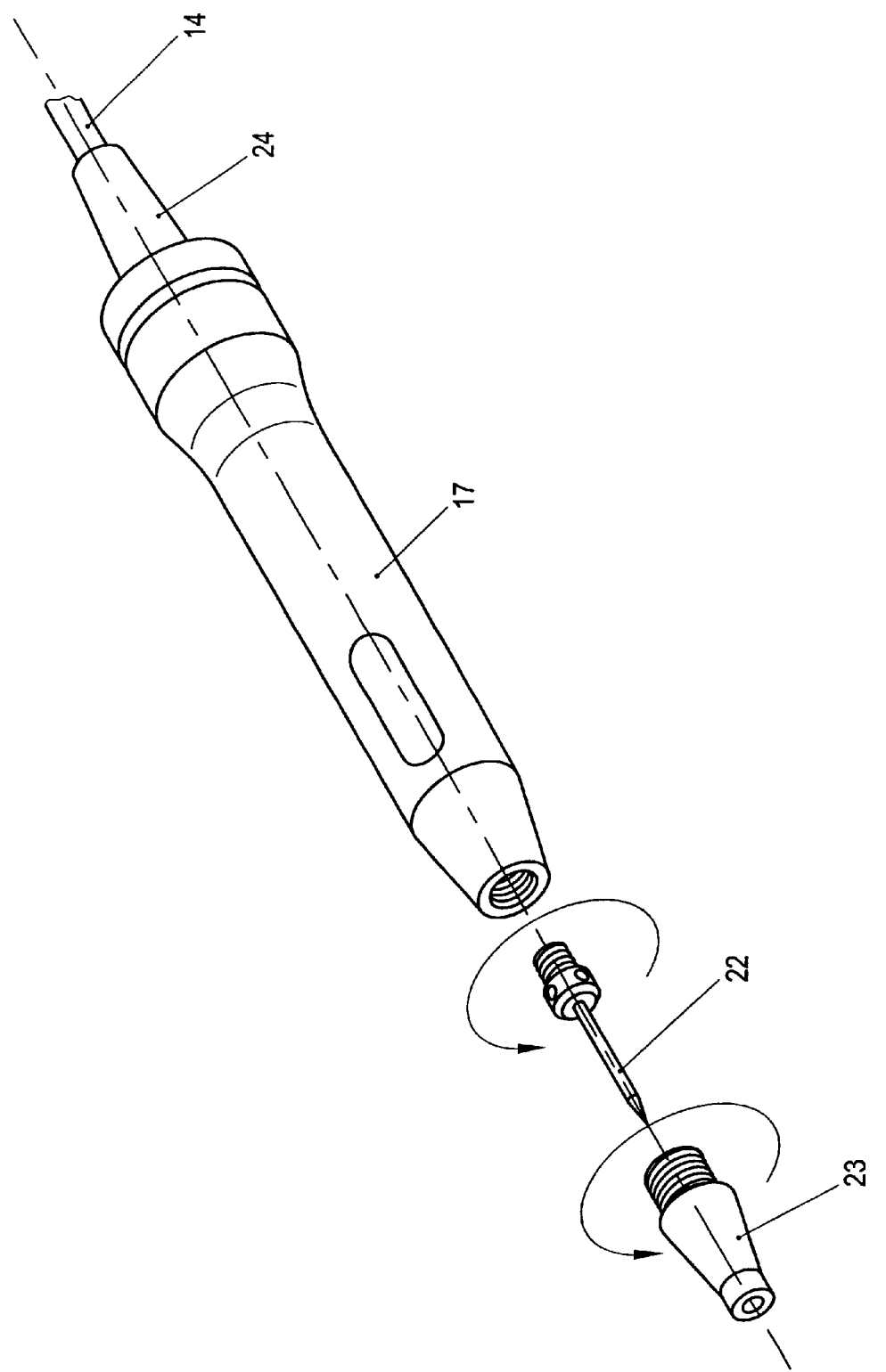
FIG. 8 is a perspective explosive view of a hand piece assembled with a screw connection according to the present invention.

The hand piece according to FIG. 8 shows a construction similar to that shown in FIGS. 5, 6 and 7. The exchangeability of the ceramic nozzle and of the metal tip is an advantageous feature associated with the embodiment of FIG. 8.

Figure 9:
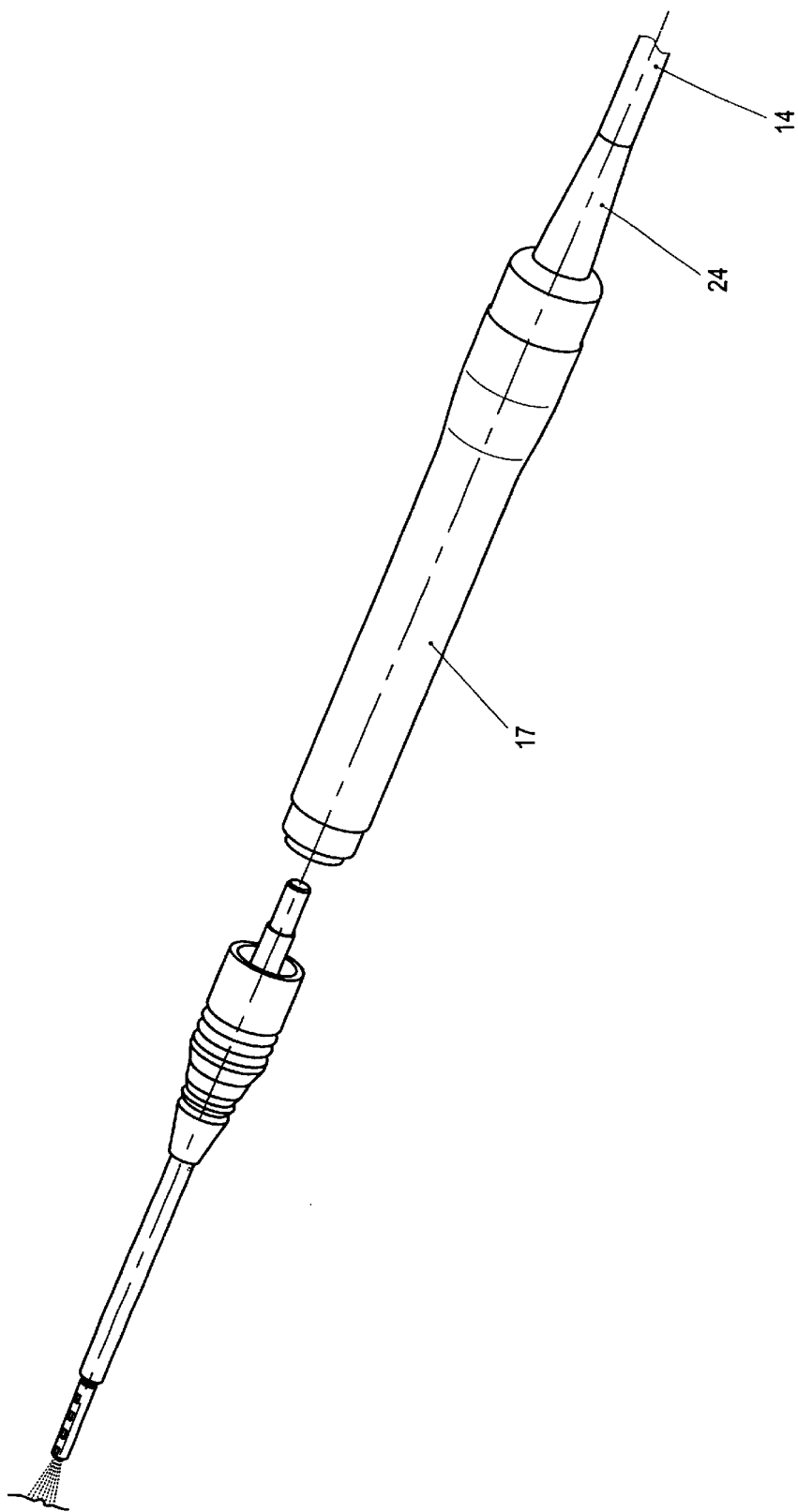
FIG. 9 is a side elevational explosion view of a hand piece including an exchangeable probe.

A handpiece with exchangeable adapters and/or probes is shown in FIG. 9. The internal construction is substantially the same as that of the embodiments shown in FIGS. 5, 6, 7 and 8. The embodiment of FIG. 9 is associated with the advantage that to plug in different application components of varying length and of varying diameter as illustrated. A screw-in coupling is provided between the part carrying the electrode tip and the part held by hand. The endoscopy probe shown in FIG. 10 is a possible application part for the hand piece of FIG. 9.

Figure 12:
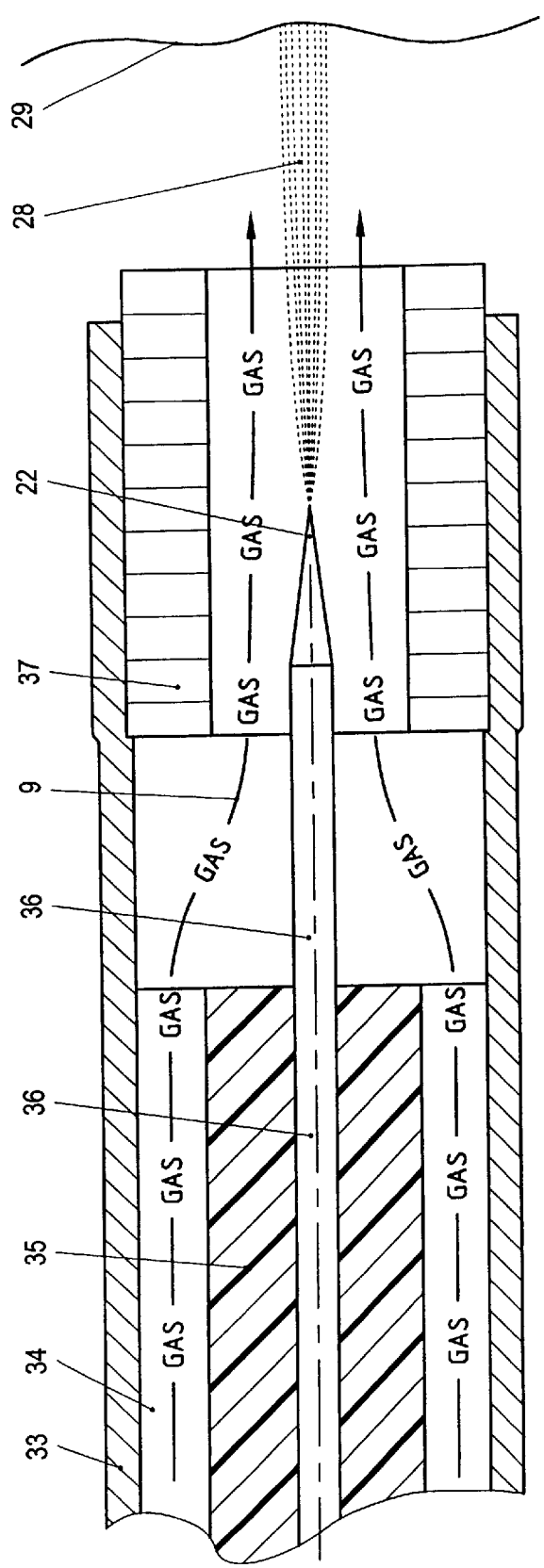
FIG. 12 is a sectional view of a second probe for endoscopy.

According to FIGS. 10, 11 and 12, the tubular shaped probe comprises an internal conductor 36 for transporting the radio frequency current. The internal conductor 36 is disposed inside of a core made of insulating plastic 35. Teflon is particular suitable for this purpose. This core is surrounded by a plastic tube 33. The gas flows only in the edge region (compare core sectional view shown in FIG. 11) through the plastic tube 33. The gas flows thereby through the edge region, where a low radio frequency field strength prevails. The gas stream joins at the distal and remote end into an inserted ceramic tube 37 (FIG. 12). The end 22 of the metal conductor 36 formed as a tip is disposed in the middle of the ceramic tube. The discharge 28 toward the tissue surface 29 is performed from this tip.

It is useful to fill the complete hollow space of the hand piece with an isolating casting compound 25 (FIG. 4) because of the necessarily high frequency voltages.

The capacity between the electrical conductor to the tip of the electrode has to be furnished as small as possible for endoscopy in order that radio frequency voltage does not drop too far, because the straight capacity of the conductor to the surface of the probe or, respectively, to the metal parts of the endoscope forms a voltage divider with the hand piece capacitor 18. This discharge current can lead to picture interferences with camera endoscopes. The high field strength in the region of the conductor presents another problem such that already ionization can occur here. Ionization occurs in particular upon use of He. The construction according to FIGS. 10, 11 and 12 reduces the effect of the discharge currents to permissible small values.

Figure 13:
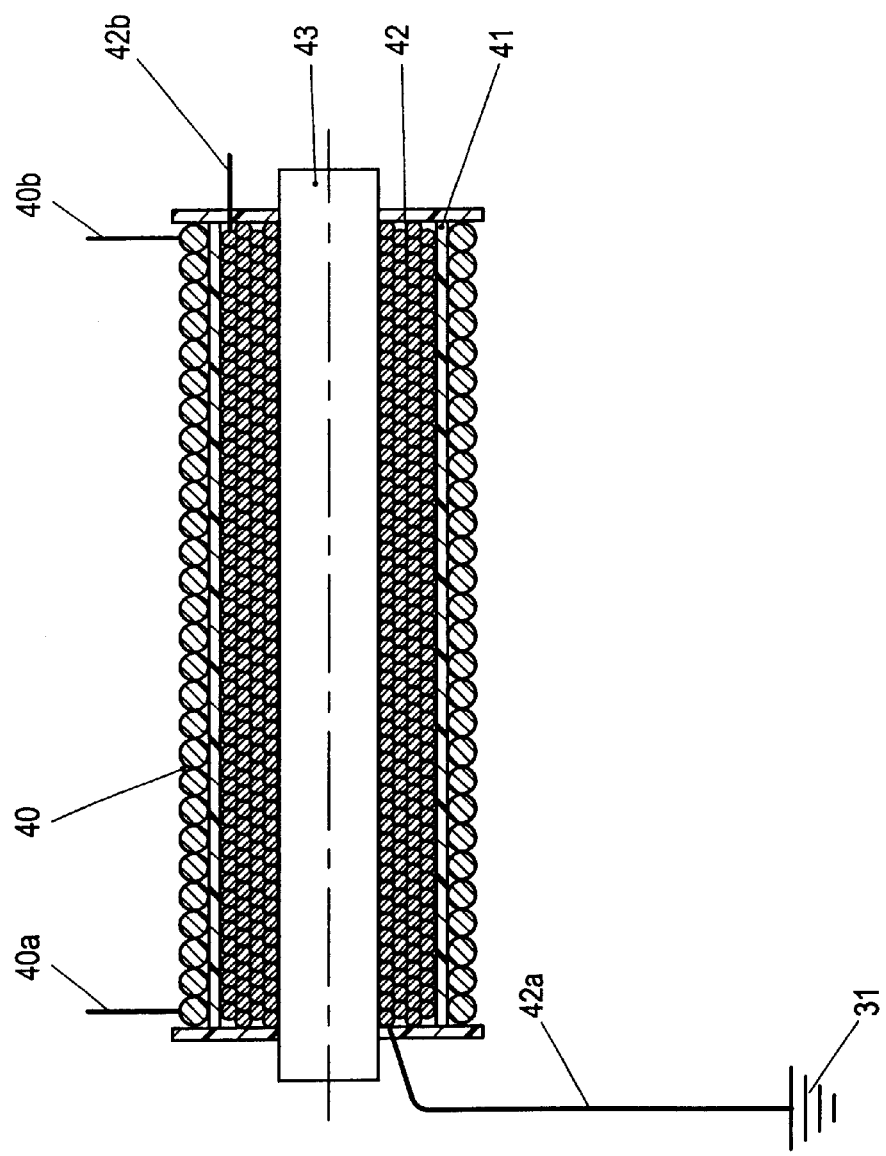
FIG. 13 is a detailed sectional view of the resonance transformer.

FIG. 13 shows the resonance transformer as an air coil without a core. The air coil comprises a primary winding 40 with a small number of windings of about 18 furnished by a relatively thick enamelled copper wire of a diameter of about 1 to 1.5 mm. The secondary winding comprises about 450 windings with a diameter of 0.2 mm. An isolating layer 41 is disposed between the primary winding and the secondary winding. The primary winding 40a, 40b is connected to the final stage as described in FIG. 1 or, respectively in FIG. 3. The start of the secondary winding 42a is connected to ground 31, while the end 42b of the secondary winding is connected to the coaxial line of the hand piece. A resonance frequency of about 350 kHz results with a capacity of the coaxial line of the hand piece cable of about 200 pF.

Figure 14:
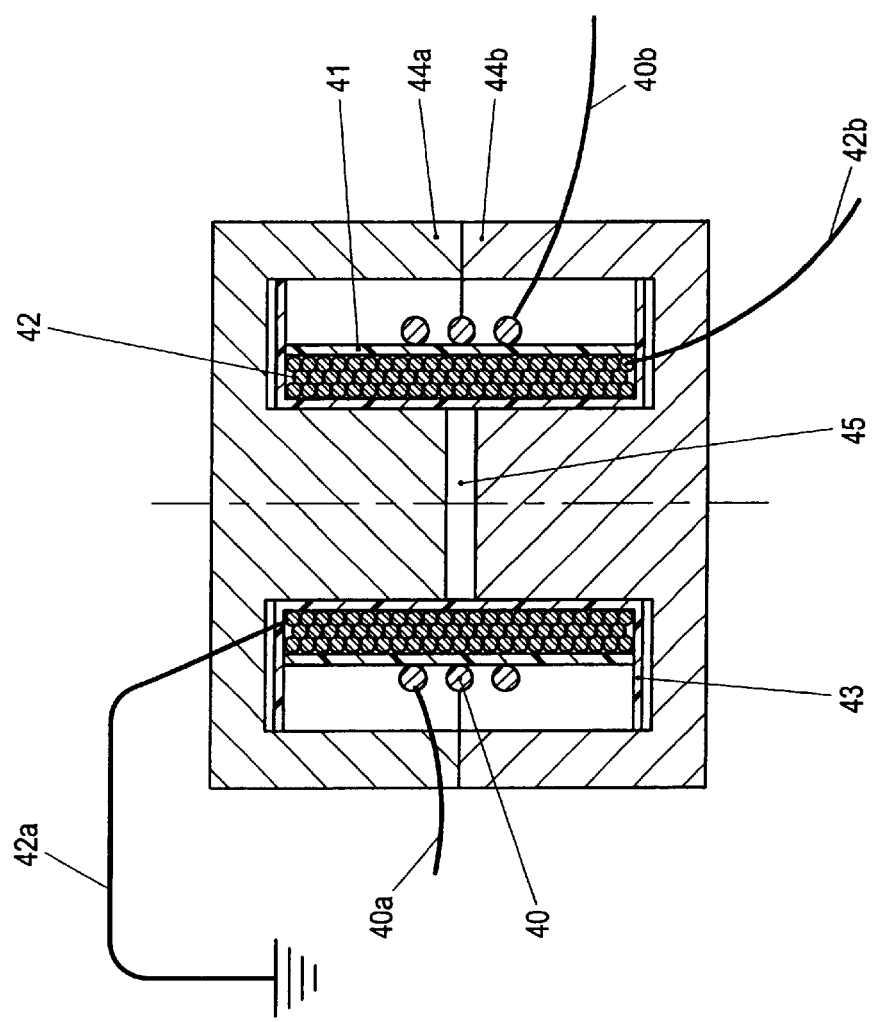
FIG. 14 is a sectional view of the resonance transformer together with a ferrite core.

FIG. 14 shows a resonance transformer with a ferrite core. The two windings 40, 42 and the coil body 43 are placed here in a subdivided ferrite core having two core halves 44a, 44b. The air gap 45 defines the magnetic resistance and defines the inductivity of the secondary coil and thus the resonance frequency of the system in case of a predetermined number of windings of the secondary coil. The advantage of this arrangement according to FIG. 14 as compared to the arrangement of FIG. 13 resides in the lower winding number of the secondary winding. About 75 windings on the secondary side are here sufficient. The primary winding 40 comprises three windings of enamelled copper wire having a diameter of 1 mm.

The advantageous features of the present radio frequency generator for surgical cuts are associated with the resonance transformer and with the capacitor disposed in the hand piece. Small peak currents are generated in comparison to conventional radio frequency surgery. No neutral electrode is required according to the construction of the present invention. The radio frequency current course corresponds to that which would result from the circuit of FIGS. 1 and 3. The hand piece capacitor preferably exhibits a capacity of from about 5 to 50 pF for delimiting the radio frequency current. The oscillator is controlled to a frequency which corresponds to the resonance frequency. The ignition coil is furnished by the resonance transformer.

Figure 15:
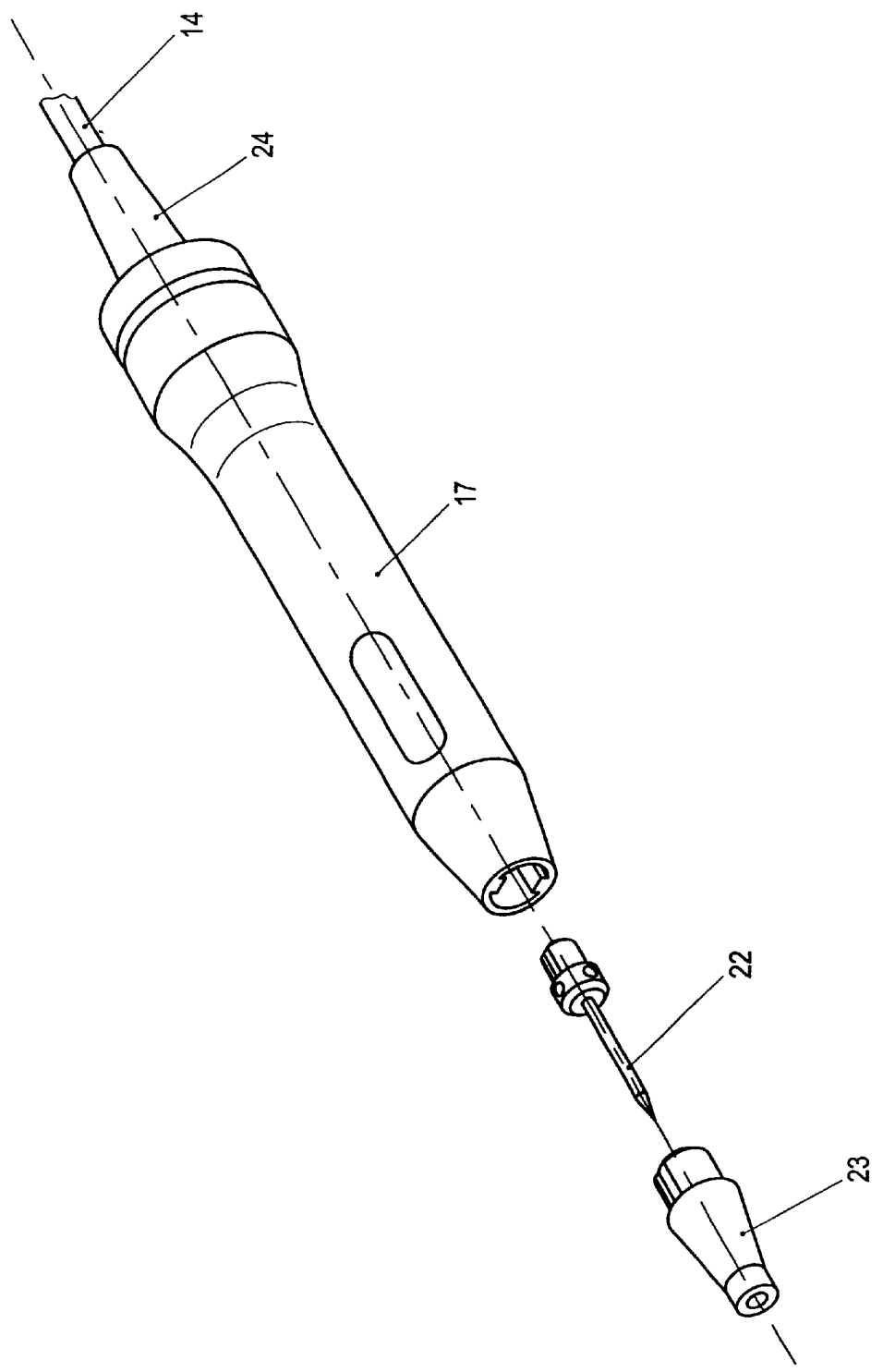
FIG. 15 is a perspective explosive view of a hand piece according to the present invention similar to the construction according to FIG. 8, however showing a plug-in connection.

The hand piece according to FIG. 15 shows a construction similar to that shown in FIGS. 5, 6, 7 and 8. The exchangeability of the ceramic nozzle and of the metal tip is furnished by a quick coupling plug-in connection for easy and reliable connection. The quick coupling is provided by guide contours extending in the longitudinal direction of the hand piece 17. A locking mechanism can be provided to define an end position after insertion of the electrode part 22 into the part held by hand 17.

Figure 16:
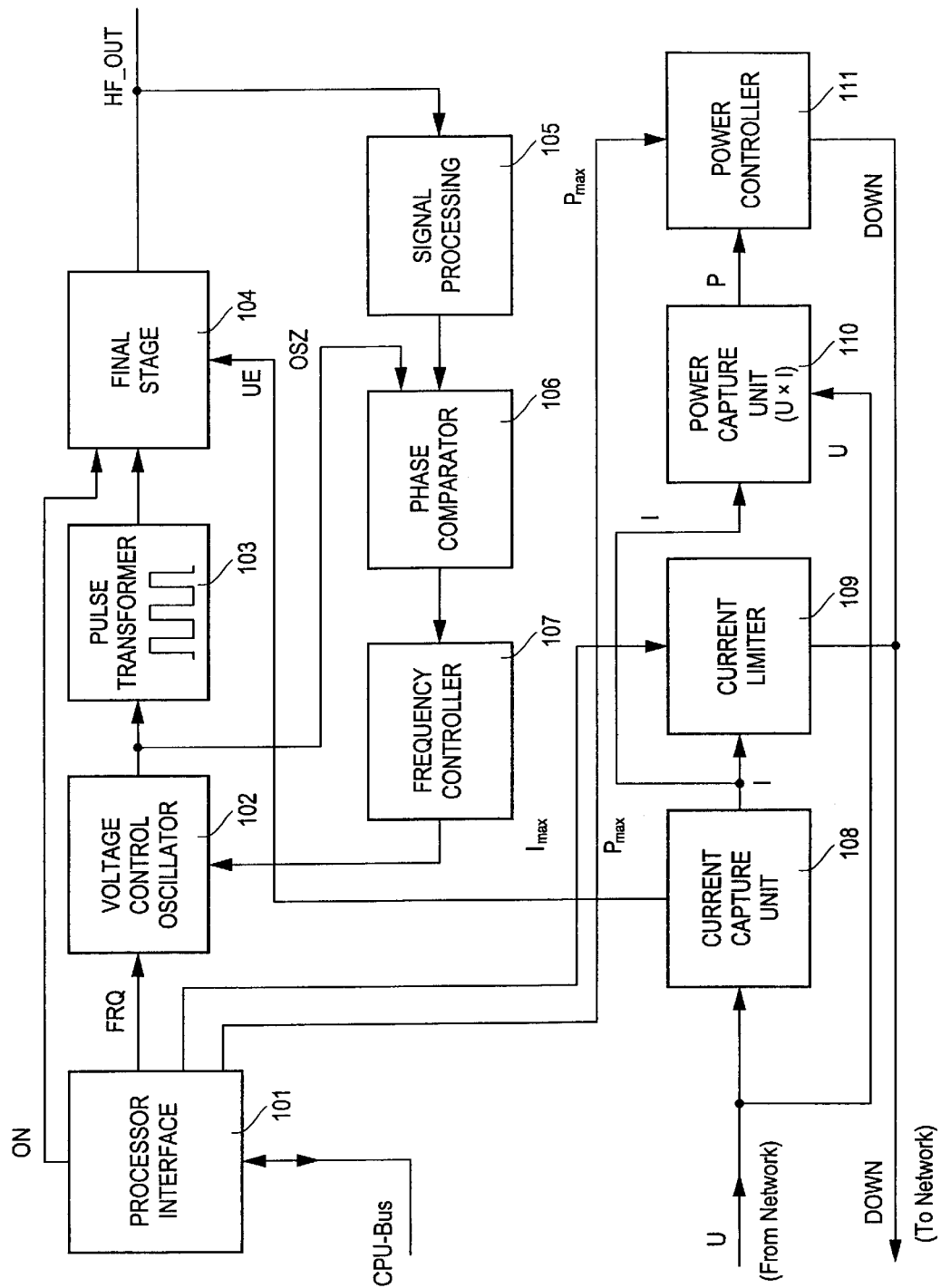
FIG. 16 is a view of a block circuit diagram illustrating a plasma generator.

FIG. 16 shows additional details of an electronic circuit for generating a radio frequency for a plasma device for surgery. The frequency is coarsely preselected through the signal (FRQ) by the processor interface 101 according to FIG. 16. The interface 101 of the processor, which delivers the analog and digital signals for parameter transfer, is controlled by a microprocessor (central processor unit bus) not described in detail here through a corresponding software.

This signal (FRQ) passes to the voltage controlled oscillator 102. The pulse transformer 103 delivers short switch-on pulses to the final stage 104, wherein the final stage 104 periodically switches the operating voltage UE to the primary coil of the ignition coil represented by a resonance transformer 6 (=signal HF-OUT). The output signal (HF-OUT) is processed at the position 105, which means the output signal (HF-OUT) is integrated and limited and then further led to a phase comparator 106.

The phase comparator 106 now compares the phases of the output signal, wherein the output signal is derived from the signal processing 105 with the phase of the oscillator 102—this is the signal OSZ—and then delivers the phase difference as an analog voltage to the frequency controller 107. The frequency controller 107 now compares the phase signal with a predetermined reference value and controls the frequency of the oscillator 102 with the aid of the signal (FRQ-TUNE) to a frequency, wherein the phase difference coincides with the predetermined reference value at the frequency. The resonance transformer is tuned to the desired resonance frequency after this procedure.

The operating voltage U passes from the power supply pack unit through a current capture unit 108 to the final stage 104. The current capture unit 108 delivers the signal I to the current limiter 109, whereby an overload of the final stage 104 is prevented. The power supply pack unit voltage U is correspondingly reduced through the control signal DOWN upon surpassing of the maximum current defined with the signal Imax.

The power capture unit 110 multiplies the actual final stage current Ia with the operating voltage U applied to the final stage and then delivers the resulting value, that is the power received by the final stage 104, to the power controller 111.

The power controller 11 now compares power signal P to the predetermined value Pmax delivered by the interface. Upon surpassing of this predetermined value Pmax, then the power supply pack unit voltage is reduced for such time through the controlled signal DOWN until the set power coincide.

The switching transistor connects the primary winding of the resonance transformer periodically to the operating voltage. This has to be performed exactly with the resonance frequency of the resonance transformer 6. The resonance frequency is correctly selected if the actual voltage at the primary winding is opposed to the operating voltage at the point in time of the switch-on process. The phase between the control signal at the switching transistor and the radio frequency signal at the resonance transformer 6 thus can be employed as a direct criteria for the correct resonance frequency.

The resonance transformer 6 comprises a primary winding with a few windings, as well as a secondary winding. The secondary winding is connected to a co-axial cable of the hand piece conduit. The inductivity of the secondary winding and the capacity of the coaxial cable form an oscillating circuit, wherein the radio frequency generator has to be tuned to the resonance frequency of the oscillating circuit. A radio frequency voltage of 2000 to 3000 volts is reached at the output of the resonance transformer. The outside conduct of the coaxial cable is additionally grounded.

The amplitude of the radio frequency voltage at the primary winding of the resonance transformer corresponds approximately to the operating voltage in case of a correct resonance frequency. The automatic control of the radio frequency output voltage is performed by varying the operating voltage. An automatic control and/or limitation of the output power is performed by a direct measurement of the discharge power at the resonance transformer.

A monitor circuit is disposed between the radio frequency generator and the resonance transformer. The monitor circuit scans, tests and monitors the delivered power of the radio frequency voltage and other parameters. The monitor circuit switches the apparatus of and generates an alarm in case of impermissible deviations for example regarding the power discharge or, respectively, the radio frequency current and other parameters.

Figure 17:
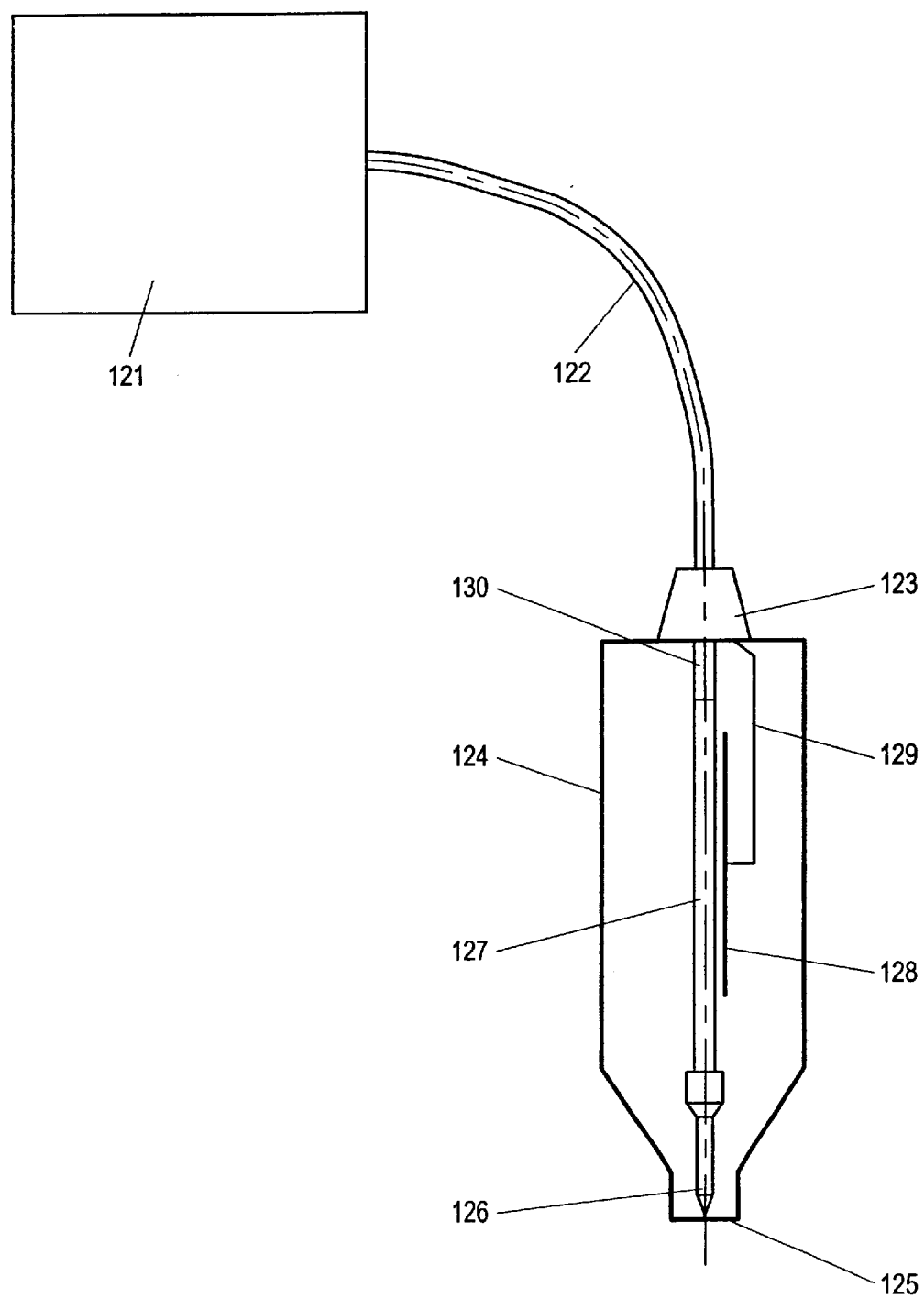
FIG. 17 is a view of a diagram illustrating the connection and construction of the hand held surgical plasma jet beam appliance.

The connection of the plasma radio frequency generator to a hand piece for surgery is illustrated in the embodiment shown in FIG. 17.

A radio frequency generator 121 is connected to a connection piece 123 attached to a hand piece 124 through a radio frequency connection cable 122 including a gas hose.

The hand piece 124 is connected to the: radio frequency generator apparatus 121 through a line 122, wherein the apparatus 121 comprises a coaxial cable and a He gas feed as well as control lines for the required operating key for activating the apparatus.

The connection cable 122 is connected to an insulated gas tube 130. The insulated gas tube 130 extends into a first capacitor part 127 including a gas tube. Then the first capacitor part 127 is disposed centrally in the elongated cylindrical hand piece 124.

A capacitor 127, 128 is disposed in the hand piece 124 wherein the capacitor 127, 128 is placed between the tip of the electrode 126 and the wire of the coaxial line 122. This capacitor 127, 128 limits the maximum radio frequency current to values below a defined and predetermined value of for example under 150 mA, wherein 150 mA is generally the maximum permissible discharge current in radio frequency surgery.

The hand piece 124 is tapered conically at its end disposed remote to the connection piece 123 and ends in a gas orifice 125. The first capacitor part 127 extends on the periphery of an ignition needle 126 running into the gas orifice 125. A second capacitor part 128 is disposed opposed to the first capacitor part 127. A connection cable 129 connects the connection piece 123 to the second capacitor part 128.

The tip 126 of the electrode together with the gas discharge is disposed in a heat resistant nozzle 125. The discharge of the gas and the electrode can also be formed as a metal tube. The plasma discharge (electric arc) starts with this electrode. The capacitor can be constructed to form a unit together with the electrode.

APPLICATION OF THE RADIO FREQUENCY GENERATOR

The advantages of the system of the present invention for coagulation of tissue include a very low penetration depth of the coagulation, very small radio frequency peak currents, or, respectively, substantially reduced current flow through the patient, since the patient does not have to be connected to a non-ground electrode, and clearly reduced electrical damages of cells disposed in the coagulation zone.

It will be understood that each of the elements described above, or two or more together, may also find a useful application in other types of radio frequency generator system configurations and surgical cutting procedures differing from the types described above.

While the invention has been illustrated and described as embodied in the context of a plasma generator for radio frequency surgical cutting, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A plasma generator for generating a cold plasma jet beam comprising a frequency tunable oscillator; a power end stage connected to the frequency tunable oscillator, wherein the oscillator controls a power end stage; a resonance transformer connected directly to the power end stage for delivering a high voltage radio frequency; a phase comparison stage having a first input and a second input, an automatic frequency control circuit connected to the phase comparison stage; an oscillator connected to the automatic frequency control circuit, and connected to the first input of the phase comparison stage, wherein the power end stage operates as a switch and is connected to the second input of the phase comparison stage;

wherein the automatic frequency control circuit (9) tunes the frequency of the rectangular pulse voltage (4), wherein the secondary winding of the resonance transformer (6) delivers a high sinusoidal radio frequency voltage with values of from about 2000 to 4000 volts.

2. A plasma generator for generating a cold plasma jet beam comprising a frequency tunable oscillator; a power end stage connected to the frequency tunable oscillator, wherein the oscillator controls a power end stage; a resonance transformer connected directly to the power end stage for delivering a high voltage radio frequency;
   a hand piece having a first end; a radio frequency connection cable including a gas hose connected to the power end stage and to the first end to the hand piece;
   wherein the hand piece comprises:
   an insulated gas tube connected to the gas hose;
   a first capacitor part including a gas tube, wherein the insulated gas tube extends into the first capacitor part including a gas tube and wherein the first capacitor part is disposed centrally in the elongated cylindrical hand piece;
   a metal tube connected to the insulated gas tube is disposed centrally in the elongated cylindrical hand piece and forms the second capacitor part;
   an electrode having a tip disposed at a second end of the hand piece disposed opposite to the first end and connected to the metal tube;
   a capacitor disposed in the hand piece wherein the capacitor is connected to the tip of the electrode and to the radio frequency connection cable.

3. A plasma generator for generating a cold plasma jet beam comprising a frequency tunable oscillator; a power end stage connected to the frequency tunable oscillator, wherein the oscillator controls a power end stage; a resonance transformer connected directly to the power end stage for delivering a high voltage radio frequency;
   a hand piece having a first end; a radio frequency connection cable including a gas hose connected to the power end stage and to the first end to the hand piece;
   wherein the hand piece comprises: an insulated gas tube connected to the radio frequency connection cable;
   a first capacitor part including a gas tube, wherein the insulated gas tube extends into the first capacitor part including a gas tube and wherein the first capacitor part is disposed centrally in the elongated cylindrical hand piece; a metal tube connected to the insulated gas tube is disposed centrally in the elongated cylindrical hand piece and forms the second capacitor part;
   an electrode having a tip disposed at a second end of the hand piece disposed opposite to the first end and connected to the metal tube;
   a capacitor disposed in the hand piece wherein the capacitor is connected to the tip of the electrode and to the radio frequency connection cable.

4. The plasma generator according to claim 3, further comprising means for changing the operating voltage, wherein a control of the delivered RF-power is performed by changing the operating voltage; and a power capture stage connected to the power end stage for capturing the power of the power end stage by multiplying an input current with an input voltage entering at the power end stage.

5. The plasma generator according to claim 4, further comprising means for measuring the radio frequency power delivered by the power end stage and connected to the power end stage.

6. The plasma generator according to claim 3, wherein the power end stage operates as a switch, and wherein the resonance transformer has a primary winding and has a secondary winding, wherein an output signal of the power end stage is delivered to the primary winding of the resonance transformer.

7. The plasma generator according to claim 6, further comprising measurement means for determining a phase difference and having a first input connected to the primary winding of the resonance transformer, and
   having a second input connected to the frequency tunable oscillator,
   wherein a phase difference between the oscillator signal and an output signal of the power end stage is measured by the measurement means, and
   wherein said output of the measurement means is connected to an input of the frequency tunable oscillator for tuning of the frequency of the frequency tunable oscillator.

8. The plasma generator according to claim 6, further comprising a control unit connected to the measurement means and to the frequency tunable oscillator for tuning the oscillator frequency relative to a resonance frequency of the resonance transformer.

9. The plasma generator according to claim 6, further comprising means for measuring the radio frequency power delivered by the resonance transformer and connected to the resonance transformer.

10. A plasma generator for generating a cold plasma jet beam comprising
   a frequency tunable oscillator;
   a power end stage connected to the frequency tunable oscillator, wherein the oscillator controls the power end stage;
   a resonance transformer connected directly to the power end stage for delivering a high voltage radio frequency;
   wherein the power end stage operates as a switch, and wherein the resonance transformer has a primary winding and has a secondary winding, wherein an output signal of the power end stage is delivered to the primary winding of the resonance transformer; and
   a hand piece, wherein a radio frequency generator is connected to the hand piece by a cable, and wherein the resonance transformer is part of the radio frequency generator.

11. A plasma generator for generating a cold plasma jet beam comprising
   a frequency tunable oscillator,
   a power end stage connected to the frequency tunable oscillator, wherein the oscillator controls the power end stage;
   a resonance transformer connected directly to the power end stage for delivering a high voltage radio frequency;
   means for changing the operating voltage, wherein a control of the delivered RF-power is performed by changing the operating voltage; and a power capture stage connected to the power end stage for capturing the power of the power end stage by multiplying an input current with an input voltage entering at the power end stage,
   wherein the frequency of the delivered RF-power is about 350 kHz.

12. A plasma generator for generating a cold plasma jet beam comprising a frequency tunable oscillator; a power end stage connected to the frequency tunable oscillator, wherein the oscillator controls a power end stage; a hand piece having a first end; a radio frequency connection cable including a gas hose connected to the power end stage and to the first end of the hand piece; wherein the hand piece comprises:
   an insulated gas tube connected to the radio frequency connection cable; a first capacitor part including a gas tube, wherein the insulated gas tube extends into the first capacitor part including a gas tube and wherein the first capacitor part is disposed centrally in the elongated cylindrical hand piece; an electrode having a tip disposed at a second end of the hand piece disposed opposite to the first end; a capacitor disposed in the hand piece wherein the capacitor is connected to the tip of the electrode and to the radio frequency connection cable; a gas orifice disposed at the second end of the hand piece, wherein the hand piece is tapered conically at its second end; an ignition needle disposed in the gas orifice, wherein the first capacitor part extends to the ignition needle; a second capacitor part disposed opposed to the first capacitor part.

13. The plasma generator according to claim 12, wherein the first capacitor part and the second capacitor part limit a maximum radio frequency current to values below under a set value from about 40 to 2000 mA.

14. The plasma generator according to claim 12, wherein the hand piece exhibits the shape of an elongated cylinder and a screw-in coupling is provided between the part carrying the electrode tip and the part held by hand.

15. A plasma generator for generating of a cold plasma jet beam wherein a plasma generator is furnished with a separate frequency tunable oscillator, wherein the separate frequency tunable oscillator controls a power end stage and wherein a resonance transformer is directly connected to the power end stage and wherein the plasma generator includes the power end stage and the resonance transformer;
wherein a phase comparison stage (10) measures a phase difference between a rectangular pulse signal and the output signal of the power end stage (5), wherein the output of the phase comparison stage is connected to an input of an automatic frequency control circuit (9);
wherein the automatic frequency control circuit (9) tunes the frequency of the rectangular pulse voltage (4), wherein the secondary winding of the resonance transformer (6) delivers a high sinusoidal radio frequency voltage with values of from about 2000 to 4000 volts.

16. The plasma generator according to claim 15, wherein an output signal of the power end stage (5) operating as a switch is delivered to the primary winding of the resonance transformer.

17. The plasma generator according to claim 15, further comprising
a hand piece having a first end;
a radio frequency connection cable including a gas hose connected to the power end stage and to the first end to the hand piece.

18. The plasma generator according to claim 17, wherein the hand piece comprises: an insulated gas tube connected to the radio frequency connection cable;
a first capacitor part including a gas tube, wherein the insulated gas tube extends into the first capacitor part including a gas tube and wherein the first capacitor part is disposed centrally in the elongated cylindrical hand piece; a metal tube connected to the insulated gas tube is disposed centrally in the elongated cylindrical hand piece and forms the second capacitor part;
an electrode having a tip disposed at a second end of the hand piece disposed opposite to the first end and connected to the metal tube;
a capacitor disposed in the hand piece wherein the capacitor is connected to the tip of the electrode and to the radio frequency connection cable.

19. The plasma generator according to claim 15, further comprising a measurement means connected to the power end stage, wherein the phase difference between the oscillator signal and the output signal of the power end stage (5) (signal RF-OUT) is measured by the measurement means for tuning of the oscillator frequency.

20. The plasma generator according to claim 19, wherein a control unit is furnished for tuning the oscillator frequency relative to the resonance frequency of the resonance transformer based on output signals of the measurement means.

21. The plasma generator according to claim 15, wherein control of the delivered RF-power and the current are performed by changing the operating voltage and wherein the power is captured by multiplying of input current and input voltage at the final stage.

22. The plasma generator according to claim 21, wherein the power control is performed by a direct measurement of the RF-power and the current delivered by the generator or, respectively, by a direct measurement of the delivered RF-power and the current of the resonance transformer.

23. A plasma generator for generating a cold plasma jet beam comprising
a casing;
a radio frequency generator for delivering a radio frequency capacitive displacement current;
a gas supply apparatus for delivering a noble gas wherein the radio frequency generator and the gas supply apparatus are placed in the casing;
a hand piece cable connected to the radio frequency generator and to the gas supply apparatus;
a hand piece connected to the hand piece cable for operating a plasma;
wherein the radio frequency generator comprises
a phase comparison stage having a first input and a second input and an automatic frequency control circuit (9) connected to the phase comparison stage;
an oscillator connected to the automatic frequency control circuit, and connected to the first input of the phase comparison stage;
a power end stage connected to the oscillator and operating as a switch, wherein the power end stage is controlled by the oscillator and connected to the second input of the phase comparison stage;
a power capture/power limiter connected to the power end stage, wherein the power capture/power limiter limits the consumption of the power and current by the power end stage;
an automatically controllable voltage source, wherein an automatically controllable voltage source delivers the voltage to the power end stage and is controlled by the capture/power limiter,
a resonance transformer having a primary winding and having a secondary winding, wherein the primary winding is connected to the second input of the phase comparison stage and to the power end stage, and wherein the primary winding is grounded:
wherein the phase comparison stage (10) measures a phase difference between the rectangular pulse signal and the output signal of the power end stage (5), wherein the output of the phase comparison stage is connected to an input of the automatic frequency control circuit (9);
wherein the automatic frequency control circuit (9) tunes the frequency of the rectangular pulse voltage (4), wherein the secondary winding of the resonance transformer (6) delivers a high sinusoidal radio frequency voltage with values of from about 2000 to 4000 volts.

24. The plasma generator according to the claim 23, wherein the power end stage (5) delivers an output signal to the primary winding of the resonance transformer (6) and to second input of the phase comparison stage (10).

25. The plasma generator according to the claim 23, wherein the oscillator (4) generates a rectangular pulse voltage signal.

26. The plasma generator according to the claim 23, wherein the power capture/power limiter (7) drives the operating voltage source (8) for automatically controlling and delimiting the output power of the power end stage (5).

27. The plasma generator according to the claim 23, wherein a first end of the hand cable (14) is connected to the radio frequency generator (3) and a second end of the hand cable is connected to the hand piece and comprising: a coaxial line (11), wherein the coaxial line (11) is connected to the secondary winding of the resonance transformer (6), and wherein the capacity (15) of the coaxial line (11) forms a resonance circuit together with the secondary winding of the resonance transformer (6); a gas tube (12), wherein the gas tube (12) is connected to the gas supply apparatus (2).

28. The plasma generator according to claim 27, wherein the hand piece (17) has a first end connected to the second end of the hand cable (14).

29. A plasma generator for generating a cold plasma jet beam comprising
a casing:
a radio frequency generator for delivering a radio frequency capacitive displacement current;
a gas supply apparatus for delivering a noble gas wherein the radio frequency generator and the gas supply apparatus are placed in the casing;
a hand piece cable connected to the radio frequency generator and to the gas supply apparatus; a hand piece connected to the hand piece cable for operating a plasma;
wherein the hand piece exhibits the shape of an elongated cylinder and comprises:
a metal tube (20), wherein the metal tube is disposed centrally in the hand piece, and wherein the metal tube is a second layer of a capacitance (18);
an electrode having a tip disposed at a second end of the hand piece and connected to the metal tube; an insulated gas line (19) slidable onto the metal tube (20) and supplying a noble gas; a conducting layer (18a) disposed onto the gas line (19), wherein the conducting layer is a first part of a capacitance (18);
a gas orifice disposed at the second end of the hand piece, wherein the hand piece is tapered conically at its second end.

30. The plasma generator according to the claim 29, wherein the radio frequency generator comprises
a phase comparison stage having a first input and a second input, and an automatic frequency control circuit (9) connected to the phase comparison stage;
an oscillator connected to the automatic frequency control circuit, and connected to the first input of the phase comparison stage;
a power end stage connected to the oscillator and operating as a switch, wherein the power end stage is controlled by the oscillator and connected to the second input of the phase comparison stage;
a power capture/power limiter connected to the power end stage, wherein the power capture/power limiter limits the consumption of the power and current by the power end stage;
an automatically controllable voltage source, wherein an automatically controllable voltage source delivers the voltage to the power end stage and is controlled by the capture/power limiter;
a resonance transformer having a primary winding and having a secondary winding, wherein the primary winding is connected to the second input of the phase comparison stage and to the power end stage, and wherein the primary winding is grounded.

31. The plasma generator according to claim 29, wherein the space between the conduct layer (18a) and the casing of the hand piece (17) is filled with an isolating casting compound (25).

32. The plasma generator according to claim 29, wherein the first conduct layer of the capacitance (18) is connected to the coaxial line (11).

33. The plasma generator according to claim 29, wherein the electrode (22) is an ignition needle disposed in the gas orifice.

34. The plasma generator according to claim 29, wherein the first conduct layer and the second conduct layer form a capacitance, wherein the capacitance limit a maximum radio frequency current to values below under a set value from about 40 to 150 mA.

35. The plasma generator according to the claim 29, wherein the power end stage (5) delivers an output signal to the primary winding of the resonance transformer (6) and to second input of the phase comparison stage (10).

36. The plasma generator according to the claim 29, wherein the power capture/power limiter (7) drives the operating voltage source (8) for automatically controlling and delimiting the output power of the power end stage (5).

37. The plasma generator according to the claim 29, wherein the phase comparison stage (10) measures a phase difference between the rectangular pulse signal and the output signal of the power end stage (5), wherein the output of the phase comparison stage is connected to an input of the automatic frequency control circuit (9).

38. The plasma generator according to the claim 37, wherein the automatic frequency control circuit (9) tunes the frequency of the rectangular pulse voltage (4), wherein the secondary winding of the resonance transformer (6) delivers a high sinusoidal radio frequency voltage with values of from about 2000 to 4000 volts.

39. A hand piece for delivering a radio frequency power and a gas flow from a plasma generator to an object comprising
a capacitor disposed between a first and a second end of the hand piece, wherein the capacitor limits the radio frequency power;
a flow gas tube connected to the first end of the hand piece for delivering the gas to the hand piece; a gas orifice disposed at the second end of the hand piece;
a metal tube connected to the flow gas tube and to the gas orifice; a coaxial line, wherein the coaxial line connected to the first end of the hand piece and to a first pole of the capacitor,
an ignition needle disposed in the gas orifice, wherein the ignition needle is connected to a second pole of the capacitor.

40. The hand piece according to claim 39, wherein the capacitor is formed by the metal tube, by an insulating layer placed on the metal tube, and by a metallic covering disposed on the insulating layer.

41. The hand piece according to claim 39, further comprising a second capacitor formed by the coaxial line for forming a resonance circuit together with a secondary winding of a resonance transformer delivering the radio frequency power to the hand piece.

* * * * *